United States Patent [19]

Seki et al.

[11] 4,225,706

[45] Sep. 30, 1980

[54] POLYCHALCOGEN ESTER OF CEPHEM COMPOUND, PROCESS FOR PREPARING THE SAME AND METHOD FOR REMOVING THE PROTECTIVE GROUP OF THE SAME

[75] Inventors: Shigeo Seki, Tokyo; Ken Nishihata, Yokohama; Satoru Nakabayashi, Yokohama; Toshinori Saito, Yokohama; Hitoshi Ikeda, Kawasaki; Nobuo Itoh, Yokohama; Shokichi Nakajima, Machida; Shunzo Fukatsu, Tokyo, all of Japan

[73] Assignee: Meiji Seika Kaisha Ltd., Tokyo, Japan

[21] Appl. No.: 898,613

[22] Filed: Apr. 21, 1978

[30] Foreign Application Priority Data

May 4, 1977 [JP] Japan .................................. 52-50688
May 4, 1977 [JP] Japan .................................. 52-50689
Aug. 31, 1977 [JP] Japan .................................. 52-103562

[51] Int. Cl.$^2$ .................. C07D 501/04; C07D 501/22; C07D 501/34; C07D 501/26
[52] U.S. Cl. ........................................ 544/16; 544/21; 544/24; 544/25; 544/26; 544/27; 544/28; 544/29; 544/30
[58] Field of Search ....................... 544/16, 29, 30, 24, 544/25, 26, 27, 28, 21

[56] References Cited

U.S. PATENT DOCUMENTS 3,862,004  1/1975  Takahashi .............................. 195/30
3,945,888  3/1976  Takahashi .............................. 195/30

OTHER PUBLICATIONS

Merck Index, p. 960, 209.
Fletcher et al., "Nomenclature of Organic Compounds", p. 171.

Primary Examiner—Mark L. Berch
Attorney, Agent, or Firm—Frishauf, Holtz, Goodman & Woodward

[57] ABSTRACT

A novel ester of a cephem compound having a carboxyl group at the 4-position in the nucleus; a process for preparing the same by reacting a cephem carboxylic acid or its salt with a halogenide; and a method for removing the protective group for the carboxyl group in the nucleus of a cephem compound by contacting it with an alcohol, or with an organic solvent in the presence of a Lewis acid.

7 Claims, No Drawings

POLYCHALCOGEN ESTER OF CEPHEM COMPOUND, PROCESS FOR PREPARING THE SAME AND METHOD FOR REMOVING THE PROTECTIVE GROUP OF THE SAME

This invention relates to an ester of a cephem compound, a process for preparing the same and a method for removing the protective group of a cephem compound.

More particularly, this invention relates to an ester of a cephem compound which is a valuable intermediate for pharmaceutically useful cephalosporin antibiotics, a process for preparing the same and a method for removing the protective group of the carboxyl group in the nucleus of a cephem compound.

When a cephem compound is coverted into another cephem compound, for instance, when a conversion is carried out with respect to the substituent at the 3- or 7-position, it is necessary to protect the carboxyl group at the 4-position and esterification thereof has generally been applied for the purpose. Although there have hetherto been known many esterifying agents and many esters obtained by the esterification, the esterification and the removal of the protective groups have not necessarily been satisfactory. Namely, conventional esterification of cephalospranic acid salts often presents problems, for example, double bond isomerization by which a mixture of the so-called $\Delta^3$-ester and $\Delta^2$-ester is obtained. In such a case, the desired $\Delta^3$-cephem isomer must be isolated by a process such as fractional crystallization. Moreover, conventional esters are unstable so that the protective group is apt to be eliminated during an intended reaction and, on the other hand, conventional esters are too stable to be removed after the reaction. In addition, conventional esterifying agents or conventional agents for removing the protective group are expensive and can not be applied for industrial purposes.

An object of this invention is to provide a novel ester of a cephem compound which can advantageously be used as an intermediate for a certain conversion of the compound with respect to the substituent at, for example, the 3- or 7-position of the cephem nucleus.

Another object of this invention is to provide an efficient and simple process for preparing the $\Delta^3$-ester exclusively mentioned above by esterification of the carboxyl group(s) of the cephem compound without isomerization of double bond in cephem nuclei.

Further object of this invention is to provide a method for removing the protective group of the carboxyl group in the nucleus of a cephem compound to form a cephem carboxylic acid by using only an alcohol, or an organic solvent in the presence of a Lewis acid.

The process and the method according to this invention have no defects accompanying conventional ones, and are very economical and simple in the procedures so that they can advantageously be applied industrially.

The novel ester of cephem compound according to this invention is represented by formula (I):

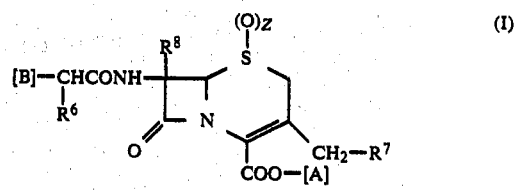

where [A] represents a group

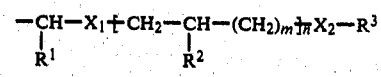

(in which $R^1$ and $R^2$ may be the same or different, each mean a hydrogen atom or a methyl group; $R^3$ means an alkyl group having 1 to 6 carbon atoms, an aryl group having 6 to 8 carbon atoms or an aralkyl group having 7 to 9 carbon atoms; $X_1$ and $X_2$ may be the same or different, each means an oxygen atom or a sulfur atom; m is an integer of 0 or 1; and n is an integer of 1 or 2); [B] represents a cyano group, a cyanomethylthio group, a trifluoromethylthio group, a substituted or unsubstituted aryl group, a substituted or unsubstituted aryloxy group, a substituted or unsubstituted aralkyl group, a substituted or unsubstituted heterocyclic group having 1 to 4 hetero atoms selected from nitrogen, oxygen and sulfur, a heterocyclic thio group, or a group

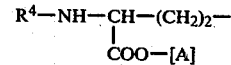

(in which [A] has the same meaning as defined above and $R^4$ means a protecting group for the amino group); $R^6$ represents a hydrogen atom, a hydroxyl group or a group $R^5$—NH—(in which $R^5$ means a hydrogen atom, an aroyl group, an alkyloxycarbonyl group, an aralkyloxycarbonyl group or a heterocyclic carbonyl group); $R^7$ represents a hydrogen atom, an azido group, an acyloxy group, a carbamoyloxy group, a heterocyclic group having 1 to 4 hetero atoms selected from nitrogen, oxygen and sulfur, an alkylthio group or a heterocyclic thio group; $R^8$ represents a hydrogen atom or a methoxy group; and Z is an integer of 0 or 1.

The substituents in the compound represented by general formula (I) may concretely be exemplified as follows. As [A], there may be mentioned $\beta$-methoxyethoxymethyl, $\beta$-methoxyethoxyethyl, $\beta$-ethoxyethoxymethyl, $\beta$-ethoxyethoxyethyl, $\beta$-propyloxyethoxymethyl, $\beta$-isopropyloxyethoxymethyl, $\beta$-t-butoxyethoxymethyl, $\beta$-phenoxyethoxymethyl, $\beta$-benzyloxyethoxymethyl, $\beta$-methoxy-$\beta$-methylethoxymethyl, $\gamma$-methoxypropyloxymethyl, $\beta$-methylthioethylthiomethyl and $\beta$-methoxyethylthiomethyl.

As [B], there may be mentioned, in addition to a cyano group, a cyanomethylthio group and a trifluoromethylthio group, a substituted or unsubstituted aryl group having 6 to 10 carbon atoms, e.g., phenyl, tolyl, chlorophenyl, bromophenyl, methoxyphenyl, hydroxyphenyl, etc.; a substituted or unsubstituted aryloxy group having 6 to 10 carbon atoms, e.g., phenoxy, tolyloxy, chlorophenoxy, bromophenoxy, methoxyphenoxy, hydroxyphenoxy, etc.; a substituted or unsubstituted aralkyl group having 7 to 11 carbon atoms, e.g., benzyl, methylbenzyl, chlorobenzyl, $\alpha$-phenethyl, etc.; a substituted or unsubstituted heterocyclic group having 1 to 4 hetero atoms selected from nitrogen; oxygen and sulfur, e.g., 2-thienyl, 3-thienyl, 2-furyl, 3-furyl, 1H-tetrazolyl, etc.; and a heterocyclic thio group, e.g., 4-pyridylthio.

As $R^4$ of a group

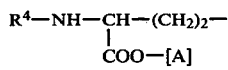

which is included in a group [B]—, there may concretely be mentioned, an alkoxycarbonyl group having 2 to 7 carbon atoms, e.g., methoxycarbonyl, ethoxycarbonyl, 5-butoxycarbonyl, etc.; an aroyl group having 7 to 10 carbon atoms, e.g., benzoyl, p-chlorobenzoyl, phthaloyl, etc.; an aralkoxycarbonyl group having 8 to 10 carbon atoms, e.g., carbobenzoxy, etc.; a haloalkanoyl group having 2 to 7 carbon atoms, e.g., chloroacetyl, etc.; an aryl group having 6 to 10 carbon atoms, e.g., 2,4-dinitrophenyl, etc.; and an aralkanoyl group having 8 to 10 carbon atoms, e.g., phenylacetyl, etc.

As $R^6$, there may be mentioned an aroylamino group having 7 to 10 carbon atoms, e.g., benzoyl amino, p-chlorobenzoyl amino, phthaloyl imino, etc.; an alkyloxy-carbonylamino group having 2 to 7 carbon atoms, e.g., t-butoxycarbonyl amino, etc.; an aralkyloxycarbonyl amino group having 8 to 10 carbon atoms, e.g., carbobenzoxyamino, etc.; and an heterocyclic carboxamino, e.g., 4-ethyl-2,3-dioxo-1-piperazinecarboxamino, etc.

As $R^7$, there may be mentioned an acyloxy group having 2 to 5 carbon atoms, e.g., acetoxy, propionyloxy, etc.; a heterocyclic group, e.g., pyridyl, carbamoylpyridyl, acetylaminopyridyl, methylthiopyridyl, etc.; an alkylthio group having 1 to 5 carbon atoms, e.g., methylthio, ethylthio, etc.; and a heterocyclic thio group, e.g., 1,3,4-thiadiazolylthio, 2-methyl-1,3,4-thiadiazolylthio, 1-methyl-tetrazolylthio, 1,2,3-triazolylthio, 1,3,4-oxadiazolylthio, etc.

The process according to this invention is a process for preparing an ester of cephem compound represented by formula (I):

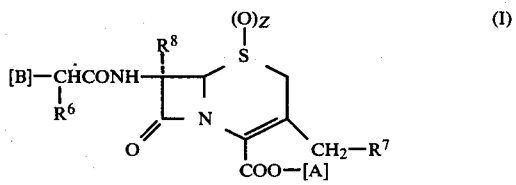

wherein [A], [B], $R^6$, $R^7$, $R^8$ and Z have the same meanings as defined above. which comprises reacting a compound represented by formula (II):

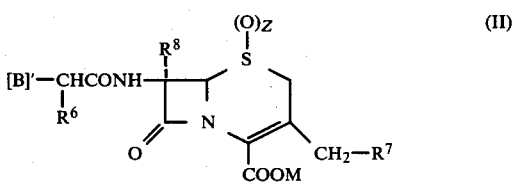

wherein [B]' represents a cyano group, a cyanomethylthio group, a trifluoromethylthio group, a substituted or unsubstituted aryl group, a substituted or unsubstituted aryloxy group, a substituted or unsubstituted aralkyl group, a substituted or unsubstituted heterocyclic group having 1 to 4 hetero atoms selected from nitrogen, oxygen and sulfur, a heterocyclic thio group or a group

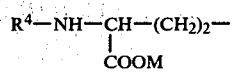

(in which $R^4$ means a protective group for the amino group; and M means a hydrogen atom, an alkali metal, an alkaline earth metal or an organic base); and $R^6$, $R^7$, $R^8$ and M have the same meanings as defined above, with a compound represented by formula (III):

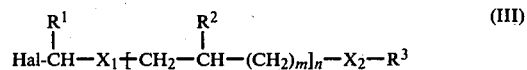

wherein $R^1$, $R^2$, $R^3$, $X_1$, $X_2$, m and n have the same meanings as defined above; and Hal represents a halogen atom such as chlorine, bromine, etc., in an inert solvent or liquid sulfur dioxide.

Namely, the process according to this invention is a process in which a compound of formula (II) is reacted with a halogenide of formula (III) in an inert solvent or liquid sulfur dioxide.

The substituents of the starting compound of formula (II) may concretely be exemplified as follows.

The substituent $R^4$ of a group

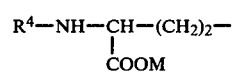

defined as a group [B] has the same meanings as mentioned in the ester of formula (I).

As [B]', there may be mentioned, in addition to a cyano group, a cyanomethylthio group, a trifluoromethylthio group and a group

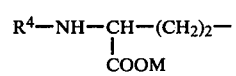

mentioned above, a substituted or unsubstituted aryl group having 6 to 10 carbon atoms, e.g., phenyl, toly, chlorophenyl, bromophenyl, methoxyphenyl, hydroxyphenyl, etc.; a substituted or unsubstituted aryloxy group having 6 to 10 carbon atoms, e.g., phenoxy, tolyloxy, chlorophenoxy, bromophenoxy, methoxyphenoxy, hydroxyphenoxy, etc.; a substituted or unsubstituted aralkyl group having 7 to 11 carbon atoms, e.g., benzyl, methylbenzyl, chlorobenzyl, α-phenethyl, etc.; a substituted or unsubstituted heterocyclic group having 1 to 4 hetero atoms selected from nitrogen, oxygen and sulfur, e.g., 2-thienyl, 3-thienyl, 2-furyl, 3-furyl, 1H-tetrazolyl, etc.; and a heterocyclic thio group, e.g., 4-pyridylthio etc.

As M, there may be mentioned an alkali metal, e.g., sodium, potassium, etc.; an alkaline earth metal, e.g., calcium, magnesium, etc.; and an organic base, specifically, an organic tertiary amine, e.g., pyridine, triethylamine tripropylamine, triisopropylamine, etc.

As the concrete examples of the compound represented by formula (III), there may be mentioned β-methoxyethoxymethyl chloride, β-methoxyethoxy bromide, β-methoxyethoxyethyl chloride, β-ethoxyethoxymethyl chloride, β-propyloxyethoxymethyl chloride, β-isopropyloxyethoxymethyl chloride, β-phenoxyethoxymethyl chloride, β-benzyloxyethoxymethyl chloride, β-methoxy-β-methylethoxymethyl chloride, γ-methoxypropyloxymethyl chloride, β-methylthioethylthiomethyl chloride, β-methoxyethylthiomethyl chloride and so on.

In cases where the esterification is to be effected in an organic solvement, the reaction is carried out in an aprotic solvent such as dimethylformamide, dimethylacetamide, dimethylsulfoxide, methylene chloride, dioxane, tetrahydrofuran and the like, at −50° C. to 100° C. for 10 minutes to 5 hours by using 1.0 to 5.0 equivalents, preferably, 1.1 to 2.0 equivalents of a halogenide represented by formula (III) against the carboxyl group(s) contained in the compound of formula (II). At this time, the reaction may be accelerated by adding an organic base such as triethylamine, pyridine and the like to the reaction medium.

In cases where the compound of formula (II) is to be esterified in liquid sulfur dioxide with a halogenide of formula (III), the reaction is conducted at a boiling point of liquid sulfur dioxide for 30 minutes to 10 hours by using 1.0 to 3.0 equivalents, preferably, 1.2 to 1.5 equivalents of a base and 1.0 to 5 equivalents, preferably, 1.5 to 2 equivalents of a compound of formula (III) against the carboxyl group(s) contained in the compound represented by formula (II).

Since the esterifying agent which is used for obtaining a novel ester of this invention has extremely high reactivity, the esterification reaction proceeds smoothly in sufficiently high velocity even below −30° C. Accordingly, the double bond isomerization which always accompanies the conventional esterification reaction of cephem compounds does not occur in the present invention. Therefore, only the desired $\Delta^3$-isomer can be obtained in high yield without any procedure for separating isomers.

The ester of a cephem compound of formula (I) which is obtained according to the process of this invention can be purified by crystallization etc., according to an ordinary method. The compound of formula (I) obtained according to this invention can be converted into another cephem compound and thereafter the protective group for the carboxyl group at the cephem nucleus can easily be removed according to the method of this invention as mentioned below.

The method for removing the protecting group of the carboxyl group is a process for preparing a cephem compound represented by formula (IV):

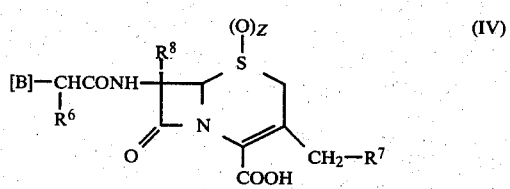

(IV)

wherein [B], $R^6$, $R^7$, $R^8$ and Z have the same meanings as defined above, or a pharmaceutically acceptable inorganic or organic salt thereof which comprises removing the protective group [A] of a cephem compound represented by formula (I):

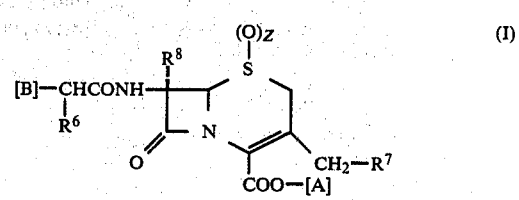

(I)

wherein [A],[B], $R^6$, $R^7$, $R^8$ and Z have the same meanings as defined above, by treating the same in an alcohol, or in an organic solvent in the presence of a Lewis acid.

The ester of formula (I) is dissolved in an alcohol. An alcohol which can be used for the purpose is not limited in particular if it dissolves the starting ester, but may be mentioned preferably a lower alcohol having 1 to 4 carbon atoms such as methanol, ethanol, n-propanol, isopropanol, n-butanol, isobutanol, sec-butanol and tert-butanol; a polyhydric alcohol such as ethylene glycol, diethylene glycol, triethylene glycol, glycerol and the like; and a methyl- or ethyl-ether of a polyhydric alcohol such as ethylene glycol monomethyl ether, ethylene glycol monoethyl ether, diethylene glycol monomethyl ether, triethylene glycol monomethyl ether and the like. The concentration of the solution is not limited in particular but may preferably be 1 to 20% by weight-/volume (abbreviated hereinafter as W/V) of the starting ester. The alcoholic solution is allowed to stand at room temperature or is heated to effect the removal of the protective group for the carboxyl group. The reaction temperature is in the range of 20° to 100° C., preferably, 40° to 70° C., and the reaction period is in the range of 30 minutes to 48 hours, preferably, 1 to 5 hours. The reaction proceeds almost quantitatively to give a carboxylic acid in high purity.

The removal of the protective group can also be effected by adding a Lewis acid to the reaction medium. In such a case, the solvent is not restricted to an alcohol and any organic solvent widely used for general purposes can also be used, if it dissolves the ester compound. As the solvent may be exemplified, in addition to the alcohols mentioned above, methylene chloride, chloroform, ethyl acetate, tetrahydrofuran, dioxane, acetone, methylethyl keton, N,N-dimethylformamide, dimethylsulfoxide and so on. As the Lewis acid may be used any one which can accept an unshared electron pair, for example, an inorganic compound such as magnesium chloride, magnesium bromide, aluminium chloride, titanium tetrachloride, ferrous chloride, ferric chloride, cobalt chloride, nickel chloride, cuprous chloride, cupric chloride, zinc chloride, zinc bromide, stannic chloride (tin tetra-chloride), etc., and the hydrates thereof; an organomethallic compound such as nickel diacetate, etc.; trifluoro-boron-etherate and so on.

The amount of the Lewis acid to be added is 0.1 to 10 equivalents, preferably, 1 to 3 equivalents against the ester compound. The Lewis acid need not be dissolved in the solvent and the reaction proceeds smoothly even when the Lewis acid is in a suspended state. The reaction temperature is in the range of 10° to 100° C., preferably, 20° to 70° C., and the reaction period is in the range of 30 minutes to 48 hours, preferably, 1 to 5 hours. In such a case, the reaction proceeds quantitatively too and the removal of the Lewis acid after reaction can readily be effected and an ester compound of high purity can simply be obtained.

Further, as a result of our trial for various reactions for removing the protective group for carboxyl groups, the present inventors have found that a diester of a dicarboxylic acid such as a diester derivative of Cephalosporin C is converted into a mono ester in which the protective group for the carboxyl group in the cephem nucleus is removed selectively and thus the ester of the cephem nucleus is more reactive than that in the side chain. Further, as a result of our careful comparison of the rate in the protective-group-removing reaction of the ester of adipic acid which was synthesized separately with that of the ester of a cephem-nucleus carboxylic acid, it was found that the rate in the protective-group-removing reaction of the cephem-nucleus carboxylic acid ester is remarkably higher than that of the adipic acid ester as in the case of the selective removal of the protective group in the diester compound mentioned above. This fact will be explained detailedly hereinbelow.

When the method of this invention is applied to a continuous manufacture of various cephalosporin antibiotics starting from Cephalosporin C, the manufacturing method thereof becomes extremely important industrially. In the continuous process, Cephalosporin C is converted, after protection of the amino group and the carboxyl group, into an iminohalide and then into an imino ether, and then the acyl group at the 7-position is exchanged with another acyl group and finally the protective group of the carboxylic acid is removed to obtain the desired cephem compound. After removal of the protective group, it is necessary to purify the crude product in the reaction mixture by extraction etc., to obtain the desired product of high purity. However, in the conventional reaction for removing the protective group of carboxyl group, the ester in the 7-position moiety eliminated by the acyl group exchange (transacylation) of Cephalosporin C is converted, together with the ester of the desired cephem compound, both into carboxylic acids. Hence, troublesome procedures have been required for removing the side-chain moiety. According to the method of this invention in which the ester of formula (I) is used as a carboxyl-group-protected compound of Cephalosporin C and the protective-group-removal of the mixture obtained after the acyl group exchange reaction (transacylation) at the 7-position is carried out by using such an alcohol as methanol, etc., only the ester of the desired cephem compound is deprotected selectively to be a free acid and the ester of the side-chain moiety is kept intact. Accordingly, the desired free acid of a cephem compound can readily be separated from the undesired ester of the side-chain moiety, and thus a cephalosporin antibiotic having extremely high purities can be obtained.

The characteristics of the method for removing the protective-group of carboxyl group according to this invention are summarized as follows:

(1) The solvent serves also as a protective-group-removing agent.
(2) The solvent or the agent for removing the protective group is readily available and is inexpensive.
(3) The reaction proceeds quantitatively under mild conditions.
(4) After-treatment can be effected with extreme ease.
(5) Since the reaction possesses high selectivity against the diester compound, etc., this characteristic can widely be applied.

Thus, it is evident that the present invention is extremely practical and industrial.

The process and the method according to this invention will be explained more detailedly by the following non-limitative examples.

EXAMPLE 1

Preparation of N-benzoylcephalosporin C di-$\beta$-methoxyethoxymethyl

In 50 ml. of N,N-dimethylformamide was dissolved 10.4 g. of N-benzoylcephalosporin C. To the resulting solution were added 4.5 g. of triethylamine and 6.2 g. of $\beta$-methoxyethoxymethyl chloride at $-30°$ C. and the resulting mixture was subjected to reaction at the same temperature for 2 hours. After completion of the reaction, the reaction mixture was extracted with 100 ml. of ethyl acetate. After washing in turn with an aqueous sodium hydrogen carbonate and water, the organic layer was dried over anhydrous magnesium sulfate. After evaporation of the ethyl acetate, isopropyl ether was added to the residue at 0° C., whereupon N-benzoylcephalosporin C di-$\beta$-methoxyethoxymethyl was precipitated.

Yield: 12.8 g. (92%).

Melting point: 115.5~117° C.

Angle of rotation (C=1.4, EtOH): $[\alpha]_D +91.2°$, $[\alpha]_{578} +106°$, $[\alpha]_{436} +225°$, $[\alpha]_{365}$ 41.5°.

Mass spectrum: 696 (molecular ion), (m/e) 597, 524, 503, 392, 370, 336.

Infrared absorption spectrum (KBr): 3300, 2960, 2900, 1790, 1740, 1655, 1535 cm$^{-1}$.

Ultraviolet absorption spectrum (EtOH): 213 ($\lambda$min.) 228 ($\lambda$max.), 265 (shoulder) nm.

Nuclear magnetic resonance spectrum (CDCl$_3$, TMS as an internal standard) $\delta$(ppm): 1.87 (multiplet), 2.06 (singlet, 3H), 2.40 (multiplet), 3.37 (singlet, 6H), 3.56 (multiplet), 3.80 (multiplet), 4.96 (AB-quartet, 2H, $\delta_{AB}=36$ Hz, J=14 Hz), 4.94 (doublet, 1H, J=4.4 Hz), 5.41 (singlet, 2H), 5.50 (singlet, 2H), 7.40 (multiplet), 7.84 (multiplet).

EXAMPLE 2

Preparation of Cepharothin

In 100 ml. of anhydrous methylene chloride was dissolved 6.96 g. of N-benzoylcephalosporin C di-$\beta$-methoxyethoxymethyl. To the resulting solution was added 3.64 g. of N,N-dimethylaniline and the mixture was cooled to $-40 \sim -50°$ C. After addition of 4.16 g. of phosphorus pentachloride thereto, the mixture was reacted for 3 hours. Further, after 10 ml. of anhydrous methanol was added thereto at the same temperature, the reaction was conducted at $-30° \sim -40°$ C. for one hour and at $-20° \sim -30°$ C. for one hour. After the mixture was cooled again to $-40°$ C., 10.9 g. of N,N-dimethylaniline and 6.4 g. of thienylacetyl chloride were added thereto and the reaction was conducted by maintaining the mixture at $-30°$ C. for 3 hours and at $-20°$ C. overnight. After reaction, the reaction mixture was concentrated under reduced pressure while maintained at 10° C. To the residue were added 100 ml. of ethyl acetate and 40 ml. of water, and the resulting mixture was adjusted to pH 1.0 with 6 N hydrochloric acid. After separation of the ethyl acetate layer, 40 ml. of water was added thereto and the pH value was adjusted to 1.0 with 6 N hydrochloric acid. After separation, the ethyl acetate layer was washed with 40 ml. of water and then concentrated to give an oily substance. The thus obtained oily substance was dissolved in 50 ml. of methanol. After the solution was refluxed under heating for 2 hours, it was concentrated under reduced pressure. The concentrate thus obtained was dissolved in 100 ml. of ethyl acetate and cooled to below 10° C. after addition of 100 ml. of water. After a saturated aqueous sodium hydrogen carbonate was added to adjust the pH value to 5.5, the aqueous layer was separated. Next, after 100 ml. of ethyl acetate was added and then 6 N hydrochloric acid was added to adjust the pH value to 3.0, the ethyl acetate layer was separated and washed with 10 ml. of water. The ethyl acetate layer was concentrated to give 20 ml. of a concentrate. To the resulting concentrate was added around 2.5 g. of dibenzylamine and the mixture was allowed to stand to give 3.6 g. of crystals of dibenzylamine salt of Cephalothin. The crystals were suspended in a mixture of 100 ml. of ethyl acetate and 50 ml. of water. The suspension was cooled and adjusted to pH 0.5 by adding 6 N hydrochloric acid. Insoluble substances precipitated were removed by filtration, and the ethyl acetate layer was separated and washed three times with 10 ml. of water. The ethyl acetate layer was concentrated, and 20 ml. of methanol was added to the residue. After addition of around 50 ml. of water, the mixture was allowed to stand under cooling to give 2.26 g. of the crystals of Cephalothin (yield: 57% based on N-benzoylcephalosporin C di-$\beta$-methoxyethoxymethyl). The physicochemical properties of the products was identical with those of an authentic sample of Cephalothin. According to a biological assay, its titre was 970 u/mg.

EXAMPLE 3

Preparation of 1-oxo-N-benzoylcephalosporin C di-$\beta$-methoxyethoxymethyl

In 50 ml. of dimethylformamide was dissolved 5.35 g. of N-benzoylcephalosporin C S-oxide, and 2.5 g. of triethylamine was added thereto. Next, after 3.75 g. of $\beta$-methoxyethoxymethyl chloride was added and the resulting mixture was stirred for 10 minutes, 50 ml. of methylene chloride was added to the mixture. After washing successively with 30 ml. of water, 30 ml. of a saturated aqueous sodium hydrogen carbonate and 30 ml. of an aqueous sodium chloride, the organic layer was dried over anhydrous magnesium sulfate and the solvent was removed under reduced pressure to give a yellow oil. To the resulting oil was added 20 ml. of ether to form a precipitate. After filtration of the precipitate, 6.23 g. of crystals of 1-oxo-N-benzoylcephalosporin C di-$\beta$-methoxyethoxymethyl was obtained.

Yield: around 88%.

Melting point: 147°~150.5° C.

Angle of rotation (C=1.4, EtOH): $[\alpha]_D+99°$, $[\alpha]_{578}+99°$, $[\alpha]_{436}+113°$, $[\alpha]_{365}+169°$.

Mass spectrum (m/e): 336, 308, 266, 246, 232.

Infrared absorption spectrum (KBr): 3300, 2945, 1785, 1735, 1650, 1530 cm$^{-1}$.

Ultraviolet absorption spectrum: 265 ($\lambda$max.), 252 ($\lambda$min.)nm.

Nuclear magnetic resonance spectrum (CDCl$_3$, TMS as an internal standard) $\delta$ (ppm): 1.87 (multiplet), 2.06 (singlet, 3H), 2.36 (multiplet), 3.35 (singlet, 3H), 3.37 (singlet, 3H), 3.56 (multiplet), 3.82 (multiplet), 4.55~4.90 (multiplet), 5.40 (singlet, 2H), 5.53 (AB-quartet, 2H, $\delta_{AB}=8$ Hz, $J_{AB}=6$ Hz), 6.01 (quartet, 1H, J=5.8 Hz, J=10 Hz), 6.97 (doublet, 1H, J=10 Hz), 7.20~7.90 (multiplet).

EXAMPLE 4

Preparation of Cephalothin

In 70 ml. of dried methylene chloride was dissolved 3.56 g. of 1-oxo-N-benzoylcephalosporin C di-$\beta$-methoxyethoxymethyl, and 3.64 g. of N,N-dimethylaniline was added thereto. After cooling the mixture to $-40°\sim-50°$ C., 3.12 g. of phosphorus pentachloride was added and the reaction was conducted for 3 hours. Further, 6 ml. of anhydrous methanol was added at the same temperature and the reaction was conducted at $-30°\sim-40°$ C. for one hour and at $-20°\sim-30°$ C. for one hour. After cooling the mixture again to $-40°$ C., 11.75 g. of N,N-dimethylaniline and the reactive derivative of thienylacetic acid prepared with 3.28 g. of sodium thienylacetate, 2.08 g. of sulfuric anhydride and 26 ml. of dimethylformamide were added thereto and the reaction was carried out at $-30°$ C. for one hour and at $-20°$ C. for 2 hours. After reaction, the resulting mixture was maintained at 0° C. and was adjusted to pH 2.0 with 6 N hydrochloric acid. After stirring for 30 minutes and subsequent separation of the methylene chloride layer, the aqueous layer was extracted with 5 ml. of methylene chloride. The methylene chloride layers were combined with each other and then concentrated. The resulting concentrate was dissolved in 30 ml. of ethyl acetate, and 20 ml. of water and 6 N hydrochloric acid were added thereto to adjust the pH value to 1.5. The ethyl acetate layer was separated, washed with water and then concentrated. The concentrate thus obtained was dissolved in 100 ml. of tetra-hydrofuran and 6 g. of zinc bromide was added thereto, and the reaction was carried out at room temperature for 6 hours. The reaction mixture was concentrated and 40 ml. of ethyl acetate was added thereto under ice-cooling. After adjusting the pH value to 3.5 with a hydrochloric acid, the ethyl acetate layer was separated and washed three times with 10 ml. of water. The ethyl acetate layer was concentrated and isopropyl ether was added to the concentrate for crystallization to give 0.98 g. (49.5%) of Cephalothin. The physicochemical properties of the product were identical with those of an authentic sample.

EXAMPLE 5

Preparation of Cephalothin $\beta$-methoxyethoxymethyl

In 20 ml. of liquid sulfur dioxide was dissolved 3.96 g. of cephalothin, and 1.2 g. of triethylamine was added thereto. Then, 1.5 g. of $\beta$-methoxyethoxymethyl chloride was added thereto. The reaction vessel was equipped with a reflux condenser cooled with dry ice-methanol and the mixture in the vessel was stirred for 2 hours at the boiling point of the reaction liquid, i.e., around $-5°$ C. Thereafter, the liquid sulfur dioxide was removed by distillation to obtain an oily substance. The oily substance was dissolved in 100 ml. of methylene chloride and washed in turn with 30 ml. of water, 30 ml. of a saturated aqueous sodium hydrogen carbonate and 30 ml. of a saturated aqueous sodium chloride. The organic layer was dried over anhydrous magnesium sulfate and the solvent, the methylene chloride was removed under reduced pressure to give a yellow oil. To the oil was added 20 ml. of ether to cause crystallization. Upon filtration, 4.11 g. of crystals of Cephalothin-methoxyethoxymethyl was obtained.

Yield: about 84%.

Melting point: 97.5°~98.5° C.

Angle of rotation (C=1, EtOH): $[\alpha]_D +138°$, $[\alpha]_{578} +155°$, $[\alpha]_{436} +302°$, $[\alpha]_{365} +595°$.

Mass spectrum: 484 (molecular ion), (m/e): 424, 351, 304, 292.

Infrared absorption spectrum (KBr): 3280, 3050, 2945, 2900, 1780, 1730, 1660, 1540 cm$^{-1}$.

Ultraviolet absorption spectrum (EtOH): 216 (λmin.), 238.5 (λmax.), 267 (shoulder) nm.

Nuclear magnetic resonance spectrum (CDCl$_3$, TMS as an internal standard) δ(ppm): 2.07 (singlet, 3H), 3.36 (singlet, 3H), 3.83 (singlet, 2H), 4.99 (AB-quartet, 2H, $\delta_{AB}$=34 Hz, $J_{AB}$=14 Hz), 4.96 (doublet, 1H, J=4.8 Hz), 5.46 (singlet, 2H), 5.83 (quartet, J=4.8 Hz, J=9 Hz), ∼6.97 (multiplet), ∼7.24 (multiplet), ∼3.5 (multiplet).

EXAMPLE 6

Preparation of Cephalothin β-methoxyethoxymethyl

In 20 ml. of dimethylformamide was dissolved 3.96 g. of Cephalothin and the solution was cooled to −30° C. Next, 1.2 g. of triethylamine and 1.5 g. of β-methoxyethoxymethyl chloride were added therto. After reaction for 30 minutes at −30° C., 50 ml. of ethyl acetate and 20 ml. of water were added to the reaction mixture. After the organic layer was separated and washed with a diluted aqueous sodium hydrogen carbonate and then with water, it was dried over anhydrous magnesium sulfate and the solvent, i.e., ethyl acetate was removed under reduced pressure to obtain a yellow oil. To the resulting oil was added 20 ml. of ether to cause crystallization. After filtration, 4.21 g. of crystals of Cephalothin β-methoxyethoxymethyl was obtained.

Yield: 87%.

EXAMPLE 7

Preparation of Cephalothin

In 50 ml. of methanol was dissolved 4.84 g. of Cephalothin β-methoxyethoxymethyl and the solution was refluxed under heating for 2 hours. The methanol was removed by distillation under reduced pressure and the residue was dissolved in 200 ml. of ethyl acetate. After washing with water, the organic layer was dried over anhydrous magnesium sulfate and the ethyl acetate was evaporated to obtain 3.80 g. of Cephalothin as crystals. Yield: 96%. The physicochemical properties of the thus obtained Cephalothin were identical with those of an authentic sample.

EXAMPLE 8

Preparation of Cephalothin

A mixture of 4.84 g. of Cephalothin β-methoxyethoxymethyl, 5.6 g. of magnesium bromide hexahydrate and 50 ml. of tetrahydrofuran was stirred at 20°∼30° C. for 4 hours. Next, the solvent, tetrahydrofuran was removed by distillation under reduced pressure, and 200 ml. of ethyl acetate and 50 ml. of water were added to the residue. After the organic layer was separated and washed with 50 ml. of water, 50 ml. of water was added thereto. After a saturated aqueous sodium hydrogen carbonate was added to adjust the pH value to 5.5, the aqueous layer was separated. To the aqueous layer was added 200 ml. of ethyl acetate and the pH value was adjusted to 3.0 with 1 N hydrochloric acid. After the organic layer was separated and washed with 30 ml. of water, it was dried over anhydrous magnesium sulfate. After concentration of the organic layer, 3.52 g. of Cephalothin was obtained as crystals. Yield: 89%. The physicochemical properties of the product thus obtained were identical with those of an authentic sample.

EXAMPLE 9

Preparation of 7-[5'-benzoylamino-5'-(β-methoxyethoxymethoxycarbonyl)-valeroamido]-3-acetoxymethyl-3-cephem-4-carboxylic acid 1-oxide After 7.12 g. of N-benzoylcephalosporin C 1-oxide di-β-methoxyethoxymethyl was refluxed in 50 ml. of methanol under heating for 2 hours, the mixture was allowed to stand at room temperature. The crystals precipitated were collected by filtration to give 3.5 g. of crystals of 7-[5'-benzoylamino-5'-(β-methoxyethoxymethoxycarbonyl)-valeroamido]-3-acetoxymethyl-3-cephem-4-carboxylic acid 1-oxide, in which the carboxy ester of the 4-position in the cephem nucleus suffered alcolysis selectively to form a free acid.

Yield: 55%.

Melting point: 145°∼146° C, (decomp.).

Elementary analysis (for C$_{27}$H$_{33}$N$_3$O$_{11}$S): Calcd.: C 52.00, H 5.33, N 6.74%. Found: C 51.86, H 5.51, N 6.59%.

Nuclear magnetic resonance spectrum (DMSO-d$_6$) β(ppm): 1.77 (multiplet, 4H), 1.86 (singlet, 3H), 2.40 (multiplet, 2H), 3.23 (singlet, 3H), 3.2∼4.0 (multiplet, 6H), 4.62 (AB-quartet, 2H), 4.42 (multiplet, 1H), 4.90 (doublet, 1H), 5.31 (AB-quartet, 2H), 5.82 (quartet), 7.4∼8.0 (multiplet, 5H).

EXAMPLE 10

Preparation of N-benzoylcephalosporin C 1-oxide

A mixture of 7.12 g. of N-benzoylcephalosporin C 1-oxide di-β-methoxyethoxymethyl, 11.2 g. of magnesium bromide hexahydrate and 50 ml. of tetrahydrofuran was stirred at 20°∼30° C. for 5 hours. The solvent, tetrahydrofuran was removed by distillation under reduced pressure and 200 ml. of methylene chloride was added to the residue. After addition of 50 ml. of water, the organic layer was separated and washed with water. Further, 50 ml. of water was added thereto and then a saturated aqueous sodium hydrogen carbonate was added to adjust the pH value to 7.0. After separation of the aqueous layer, 200 ml. of methylene chloride was added thereto and the pH value was adjusted to 3.0 with 6N hydrochloric acid. After the organic layer was separated and washed with 20 ml. of water, it was dried over anhydrous magnesium sulfate and then concentrated. To the resulting concentrate was added isopropyl ether to obtain 4.3 g. of crystals of N-benzoylcephalosporin C 1-oxide. Yield: 80%. The physicochemical properties of the crystals were identical with those of an authentic sample of N-benzoylcephalosporin C 1-oxide.

EXAMPLE 11

Preparation of N-benzoylcephalosporin C

According to the same procedure as in Example 10, the reaction was carried out by using 6.96 g. of N-benzoylcephalosporin C di-β-methoxyethoxymethyl, 11.2 g. of magnesium bromide hexahydrate and 50 ml. of tetrahydrofuran. After treatment as in Example 10, 4.26 g. of crystals of N-benzoylcephalosporin C was obtained. Yield: 82%. The physicochemical properties of this crystals were identical with those of an authentic N-benzoylcephalosporin C.

EXAMPLE 12

Preparation of β-methoxyethoxymethyl 7-(phenoxyacetamido)-3-desacetoxy-cephalosporanate According to the same procedure as in Example 6, 3.5 g. of β-methoxyethoxymethyl 7-(phenoxyacetamido)-3-desacetoxycephalosporanate was obtained starting from 3.48 g. of 7-(phenoxyacetamido)-3-desacetoxycephalosporanic acid, 2.5 g. of triethylamine and 1.87 g. of β-methoxyethoxymethyl chloride.

Yield: 91%.

Melting point: 93°~95° C.

Angle of rotation (C=1.1, EtOH): $[\alpha]_D + 104°$, $[\alpha]_{578} + 113°$, $[\alpha]_{436} + 235°$, $[\alpha]_{356} + 400°$.

Mass spectrum: 436 (Molecular ion), (m/e): 331, 329, 280, 275, 246.

Infrared absorption spectrum (KBr): 3250, 3050, 2920, 1770, 1750, 1710, 1670 cm$^{-1}$.

Ultraviolet absorption spectrum (EtOH): 323 (λmin.), 260 (λmax.) nm.

Nuclear magnetic resonance spectrum (CDCl$_3$, TMS as an internal standard) δ(ppm): 2.16 (singlet, 3H), 3.37 (AB-quartet, $\beta_{AB}=26$ Hz, $J_{AB}=18$ Hz, 2H), 3.38 (singlet, 3H), 3.55 (multiplet, 2H), 3.86 (multiplet, 2H), 4.56 (singlet, 2H), 5.01 (doublet, J=4.2 Hz, 1H), 5.47 (AB-quartet, $\beta_{AB}=7$ Hz, $J_{AB}=6$ Hz), 5.84 (quartet, J=4.2 Hz, J=9 Hz), 6.8~7.50 (multiplet, 5H).

EXAMPLE 13

Preparation of N-t-butoxycarbonylcephalexin β-methoxyethoxymethyl

According to the same procedure as in Example 6, 4.87 g. of N-t-butoxycarbonylcephalexin β-methoxyethoxymethyl was obtained starting from 4.47 g. of N-t-butoxycarbonyl-cephalexin, 1.5 g. of triethylamine and 1.87 g. of β-methoxyethoxymethyl chloride.

Yield: 91%.

Melting point: 106°~108.5° C.

Infrared absorption spectrum (Nujol): 3320, 1775, 1725, 1688, 1660 cm$^{-1}$.

Nuclear magnetic resonance spectrum (CDCl$_3$, TMS as an internal standard) β(ppm): 1.53 (singlet, 9H), 2.07 (singlet, 3H), 3.3 (singlet, 3H), 3.0~4.0 (multiplet, 6H), 4.82 (doublet, 1H, J=4.5 Hz), 5.12 (doublet, 1H, J=6 Hz), 5.18 (singlet, 2H), 5.63 (quartet, 1H, J=4.5 Hz, J=9 Hz), 6.76 (doublet, 1H, 9 Hz), 7.2 (singlet, 5H).

EXAMPLE 14

Preparation of N-t-butoxycarbonylcephalexin

In 50 ml. of methanol was dissolved 5.35 g. of N-t-butoxycarbonylcephalexinβ-methoxyethoxymethyl, and the resulting mixture was refluxed under heating for 6 hours. After the methanol was removed by distillation under reduced pressure, the residue was dissolved in 200 ml. of ethyl acetate. After washing with 50 ml. of water, the organic layer was dried over anhydrous magnesium sulfate. After concentration, isopropyl ether was added to the residue to obtain 3.9 g. of crystals of N-t-butoxycarbonylcephalexin. Yield: 87%. Cephalexin which was obtained from the crystals by removing the protective group for an amino group according to an ordinary method was identical with an authentic sample of Cephalexin with respect to the physicochemical properties.

EXAMPLE 15

Preparation of Cefazolin β-methoxyethoxymethyl

According to the same procedure as in Example 7, 0.89 g. of Cefazolin β-methoxyethoxymethyl was obtained starting from 1 g. of Cefazolin sodium and 0.4 g. of β-methoxyethoxymethyl chloride.

Yield: 88%.

Melting point: 108°~110° C. (decomp.).

Infrared absorption spectrum (Nujol): 1775, 1710, 1695, 1630 cm$^{-1}$.

Nuclear magnetic resonance spectrum (DMSO-d$_6$, TMS as an internal standard) δ(ppm): 2.71 (singlet, 3H), 3.28 (singlet, 3H), 3.2~3.9 (multiplet, 6H), 4.42 (AB-quartet, $\delta_{AB}=38$ Hz, $J_{AB}=14$ Hz), 2H), 5.19 (doublet, J=5 Hz, 1H), 5.40 (singlet, 2H), 5.46 (AB-quartet, $\delta_{AB}=10$ Hz, $J_{AB}=6$ Hz), 5.81 (quartet, J=5 Hz, 8.5 Hz, 1H), 9.38 (singlet, 1H), 9.54 (doublet, J=8 Hz, 1H).

EXAMPLE 16

Preparation of Cefazolin

According to the same procedure as in Example 15, 2.7 g. of Cefazoline β-methoxyethoxymethyl and 100 ml. of methanol were subjected to reaction to give 1.88 g. (83%) of Cefazolin. The sodium salt obtained from the crystals according to an ordinary method showed the same physicochemical properties as those of an authentic sample of Cefazoline sodium salt.

EXAMPLE 17

Preparation of Cephalothin β-methoxyethoxymethyl

To the suspension of 20 ml. of dimethylformamide and 4.18 g. of Cephalothin sodium was added 1.5 g. of β-methoxyethoxymethyl chloride. After the reaction mixture was stirred for 5 hours at room temperature, 50 ml. of ethylacetate and 20 ml. of water were added to the reaction mixture. After the organic layer was separated and washed with a diluted aqueous sodium hydrogen carbonate and then with water, it was dried over anhydrous magnesium sulfate and the solvent, i.e., ethyl acetate was removed under reduced pressure to obtain a yellow oil. To the resulting oil was added 20 ml. of ether to cause crystallization. After filtration, 3.92 g. of crystals of Cephalothin β-methoxyethoxylmethyl was obtained.

Yield: 81%.

What is claimed is:

1. An ester of a cephem compound represented by the formula:

B—CHCONH—[cephem nucleus with $R^8$, $(O)_z$, S, N, CH$_2$—$R^7$, COO—A]
|
$R^6$ wherein A is selected from the group consisting of β-methoxyethoxy-methyl, β-methoxyethoxyethyl, β-ethoxyethoxymethyl, β-ethoxyethoxy-ethyl, β-propyloxyethoxymethyl, β-isopropyloxyethoxymethyl, β-t-butoxyethoxymethyl, β-phenoxyethoxymethyl, β-benzyloxyethoxymethyl, β-methoxy-β-methylethoxymethyl, γ-methoxypropyloxymethyl, β-methylthioethylthiomethyl and β-methoxyethylthiomethyl;

B is selected from the group consisting of cyano, cyanomethylthio, trifluoromethylthio, phenyl, tolyl, chlorophenyl, bromophenyl, methoxyphenyl, hydroxyphenyl, phenoxy, tolyloxy, chlorophenoxy, bromophenoxy, methoxyphenoxy, hydroxyphenoxy, benzyl, methyl-benzyl, chlorobenzyl, α-phenethyl, 2-thienyl, 3-thienyl, 2-furyl, 3-furyl, 1H-tetrazolyl, 4-pyridylthio, and

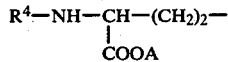

wherein R⁴ is selected from the group consisting of methoxycarbonyl, ethoxycarbonyl, 5-butoxycarbonyl, benzoyl, p-chlorobenzoyl, phthaloyl, carbobenzoxy, chloroacetyl, 2,4-dinitrophenyl, phenylacetyl, and A is the same as defined above;

R⁶ is selected from the group consisting of hydrogen, hydroxyl, benzoyl amino, p-chlorobenzoyl amino, phthalimido, t-butoxycarbonyl amino, carbobenzoxyamino;

R⁷ is selected from the group consisting of a hydrogen atom, acetoxy, propionyloxy, pyridyl, carbamoylpyridyl, acetylaminopyridyl, methylthiopyridyl, methylthio, ethylthio, 1,3,4-thiadiazolylthio, 2-methyl-1,3,4-thiadiazolylthio, 1-methyltetrazolylthio, 1,2,3-triazolylthio, and 1,3,4-oxadiazolylthio;

R⁸ is hydrogen or a methoxy group; and

Z is 0 or 1.

2. N-benzoylcephalosporin C di-β-methoxyethoxymethyl of the formula of claim 1.

3. Cephalothin β-methoxyethoxymethyl of the formula of claim 1.

4. N-benzoylcephalosporin C 1-oxide di-β-methoxyethoxymethyl of the formula of claim 1.

5. β-methoxyethoxymethyl 7-(phenoxyacetamido)-3-desacetoxycephalosporanate of the formula of claim 1.

6. N-t-butoxycarbonylcephalexin β-methoxyethoxymethyl of the formula of claim 1.

7. Cefazolin β-methoxyethoxymethyl of the formula of claim 1.

* * * * *